United States Patent
Choi et al.

(10) Patent No.: US 10,946,053 B2
(45) Date of Patent: *Mar. 16, 2021

(54) **COMPOSITION CONTAINING MIXED EXTRACT OF MULBERRY AND *PORIA COCOS* BARK FOR PREVENTING, IMPROVING OR TREATING NEURODEGENERATIVE DISORDERS**

(71) Applicant: NeuroBo Pharmaceuticals, Inc., Boston, MA (US)

(72) Inventors: Sang Zin Choi, Suwon-si (KR); Mi Won Sohn, Yongin-si (KR); Hyo Sang Go, Seongnam-si (KR); Ja Young Ryu, Seoul (KR); Jin Seok Jeong, Seoul (KR); Song Hyen Choi, Suwon-si (KR); Eun Jin Kim, Seoul (KR); Young Woong Cho, Suwon-si (KR); So Young Kim, Seoul (KR)

(73) Assignee: NeuroBo Pharmaceuticals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/820,639

(22) Filed: Mar. 16, 2020

(65) Prior Publication Data

US 2020/0289594 A1    Sep. 17, 2020

Related U.S. Application Data

(63) Continuation of application No. 15/535,489, filed as application No. PCT/KR2015/013134 on Dec. 3, 2015, now Pat. No. 10,588,927.

(30) Foreign Application Priority Data

Dec. 19, 2014  (KR) .................. 10-2014-0184854

(51) Int. Cl.
| | | |
|---|---|---|
| A61K 36/076 | (2006.01) | |
| A61K 36/605 | (2006.01) | |
| A61P 25/28 | (2006.01) | |
| A61K 9/00 | (2006.01) | |

(52) U.S. Cl.
CPC .............. *A61K 36/076* (2013.01); *A61K 9/00* (2013.01); *A61K 36/605* (2013.01); *A61P 25/28* (2018.01)

(58) Field of Classification Search
None
See application file for complete search history.

(56) References Cited

U.S. PATENT DOCUMENTS

| | | |
|---|---|---|
| 9,012,481 B2 | 4/2015 | Hahn et al. |
| 10,588,927 B2 | 3/2020 | Choi et al. |
| 2010/0184955 A1 | 7/2010 | Kim et al. |
| 2010/0285002 A1* | 11/2010 | Peer .................. A61P 29/00 424/130.1 |
| 2010/0316741 A1 | 12/2010 | Kim et al. |
| 2011/0319456 A1 | 12/2011 | Hahn et al. |
| 2018/0256658 A1 | 9/2018 | Choi et al. |

FOREIGN PATENT DOCUMENTS

| | | | |
|---|---|---|---|
| CN | 101152554 A | 4/2008 | |
| CN | 102133351 * | 3/2011 | ........... A61K 36/899 |
| CN | 102133242 A | 7/2011 | |
| CN | 102133351 | 7/2011 | |
| CN | 103393809 A | 11/2013 | |
| CN | 10413891 A | 9/2014 | |
| EP | 1997902681 | 11/1999 | |
| EP | 0970702 A1 | 1/2000 | |
| EP | 2929888 A1 | 10/2015 | |
| EP | 2929888 * | 10/2018 | ........... A61K 36/899 |
| JP | 2012-514032 A | 6/2012 | |
| JP | 2013234178 | 11/2013 | |
| KR | 20050092292 A | 9/2005 | |
| KR | 10-0526628 | 11/2005 | |
| KR | 10-2010-0070514 | 6/2010 | |
| KR | 10-2011-0070514 | 6/2010 | |
| KR | 20100070514 | 6/2010 | |
| KR | 10-1072662 | 10/2011 | |
| KR | 10-2011-0119983 | 11/2011 | |
| KR | 101251866 * | 7/2012 | ............. A61K 36/60 |
| KR | 10-1251866 | 4/2013 | |

(Continued)

OTHER PUBLICATIONS

Vattakatuchery "Acetylcholinesterase inhibitors in cognitive impairment in Huntington's disease: A brief review" World J Psychiatr Sep. 22, 2013; 3(3): 62-64 (Year: 2013).*
Rios "Chemical Constituents and Pharmacological Properties of Poria cocos" Planta Med 2011; 77: 681-691 (Year: 2011).*
Borten "Fu Ling" accessed from chineseherbinfo.com on Feb. 7, 2019 (Year: 2012).*
Lee "Anti-inflalnmatory activity of the sderotia of edible fungus, Poria cocos Wolf and their active lanostane triter" J Functional foods 32:27-36 (Year: 2017).*
Machine translation of CN 102133351 accessed from patents.google.com on Nov. 27, 2018 (Year: 2012).*
Wikipedia "wolfiporia extensa" accessed from wikipedia.org on Nov. 27, 2018 (Year: 2018).*
Machine translation of KR 101251866 accessed from patents.google.com on Nov. 27, 2018 (Year: 2018).*

(Continued)

*Primary Examiner* — Adam Weidner
(74) *Attorney, Agent, or Firm* — Sterne, Kessler, Goldstein & Fox P.L.L.C.

(57) ABSTRACT

The present invention relates to a composition comprising the mixed extract of mulberry and *Poria cocos* peel for preventing, improving or treating neurodegenerative disorders. The mixed extract of mulberry and *Poria cocos* peel which is the active ingredients contained in the composition of the present invention, has a memory improving activity through inhibiting of acetylcholine esterase and a neuroprotective effects and neuron protection by inhibiting the formation of beta amyloid and tau phosphorylation and promoting NGF production. Thus, the present invention may be useful as a pharmaceutical composition for preventing or treating degenerative neurological diseases, or as a health food for the above purpose.

7 Claims, 1 Drawing Sheet

(56) References Cited

FOREIGN PATENT DOCUMENTS

| KR | 10-2014-0074146 | | 6/2014 | |
|---|---|---|---|---|
| KR | 2007 0111846 A | | 11/2017 | |
| WO | WO 1997-29764 | | 8/1997 | |
| WO | WO 1997/29764 A1 | | 8/1997 | |
| WO | WO 2009/091130 A2 | | 7/2009 | |
| WO | WO 2014088200 | * | 6/2014 | ........... A61K 36/899 |
| WO | WO 2014088200 A1 | | 6/2014 | |
| WO | WO 2016-099055 A1 | | 6/2016 | |

OTHER PUBLICATIONS

Jean-Francois Emard et al., Neurodegenerative Diseases and Risk Factors: A Literature Review, Soc. Sci. Med. vol. 40. No. 6, pp. 847-858, Mar. 1995.

Jean C. Augustinack et al., "Specific tau phosphorylation sites correlate with severity of neuronal cytopathology in Alzheimer's disease", Acta. Neuropathol., 103, 26-35, Published online: Oct. 26, 2001.

Lee et al., "Neurodegenerative Tauopathies", Annu. Rev. Neurosci., 24, 1121-1159, Mar. 2001.

Bergeron et al., "Cortical Degeneration in Progressive Supranuclear Palsy. A comparison with cortical_Basal Ganglionic degeneration", J. Neuropathol. Exp. Neurol., 56, 726-734, Jun. 1997.

Bugiani et al., "Frontotemporal Dementia and Corticobasal Degeneration in a Family with a P301 S Mutation in Tau", J. Neuropathol. Exp. Neurol., 58, 667-677, Jun. 1999.

Delacourte et al.,"Vulnerable Neuronal Subsets in Alzheimer's and Pick's Disease Are Distinguished by Their T Isoform Distribution and Phosphorylation", Ann. Neurol., 43, 193-204, Feb. 1998.

Ittner and Gotz, "Amyloid-β and tau—a toxic pas de deux in Alzheimer's disease", Nat. Rev. Neurosci., 12, 67-72, Feb. 2011.

W. Fischer et al., "Amelioration of cholinergic neuron atrophy and spatial memory impairment in aged rats by nerve growth factor", Nature., Sep. 1987; 329(6134): 65-8.

M. Sendtner et al., "Brain-derived neurotrophic factor prevents the death of motoneurons in newborn rats after nerve section", Nature., Dec. 1992; 360(6406):757-9.

Hiroshi Mitsumoto et al., "Arrest of Motor Neuron Disease in wobbler Mice Cotreated with CNTF and BDNF", Science. Aug. 1994; 265(5175):1107-10.

Ling Hui, "Evaluation of the chemotherapeutic and chemopreventive potential of triterpenoids from Peria cocos", doctoral thesis of department of pharmacy, National University of Singapore, 2010.

Takaaki tai et al.,"Triterpenes from the surface layer of Peria cocos", Phytochem, vol. 39, No. 5, pp. 1165-1169, Jul. 1995.

Ying-Yong Zhao et al., "Urinary metabonomic study of the surface layer of Peria cocos as an effective treatment for chronic renal injury in rats", Journal of Ethnopharmacology, vol. 148, No. 2, 403-410, Available online Apr. 21, 2013.

Sandhya Joshi et al., "Classification of Neurodegenerative Disorders Based on Major Risk Factors Employing Machine Learning Techniques", International Journal of Engineering and Technology, vol. 2, No. 4, Aug. 2010.

Lin et al. "Traditional Chinese Medicine for senile Dementia," Evidence-Based Complementary and Alternative Medicine, vol. 2012 (Jan. 2012).

May et al. "Chinese Herbs for Memory Disorders: A Review and Systematic Analysis of Classical Herbal Literature," J Acupunct Meridian Stud., 6(1) :2-11 (2011).

Park et al. "Poria cocos water extract (PCW) protects PC12 neuronal cells from beta-amyloid-induced cell death through antioxidant and antiapoptotic functions", Pharmazie. 64(11):760-4 (2009).

Final Office Action dated Mar. 4, 2019, in U.S. Appl. No. 15/535,478, Choi et al., filed Dec. 3, 2015 (Int'l Filing Date).

Final Office Action dated Oct. 19, 2018, in U.S. Appl. No. 15/535,478, Choi et al., filed Dec. 3, 2015 (Int'l Filing Date).

Final Office Action dated Apr. 5, 2018, in U.S. Appl. No. 15/535,478, Choi et al., filed Dec. 3, 2015 (Int'l Filing Date).

Huang, H-P., et al., "Mulberry and its Bioactive Compounds, the Chemoprevention Effects and Molecular Mechanisms in Vitro and In Vivo," J. Tradit Complement Med 3(1):7-15, Wolters Kluwer—Medknow Publications, India (Jan. 2013).

Song, Z., et al., "The Isolation, Identification, and Determination of Dehydrotumulosic Acid in Poria cocos," Anal Sci 18(5):529-531, Japanese Society for Analytical Chemistry, Japan (2002).

Subash, S., et al., "Neuroprotective effects of berry fruits on neurodegenerative diseases," Neuro Regen Res 9(16):1557-1566, Wolters Kluwer—Medknow Publications, India (Aug. 2014).

Bai, J., "Healthy Diet Regimen for Patients with Cardiovascular and Cerebrovascular Diseases/Chief," Book Series of Food Therapy of Light Industry Press, 1 e., 4p., China Light Industry Press, China (2003).

Huang, T., "Business Opportunities in Food Development of Mulberry," China Agricultural Information 8:4p., China (2006).

Wei, J., "Modern research on Plant Medicine and Famous Chinese Herbal Medicine in Yunnan in Materia medica of South Yunman (Dian Nan Ben Cao)," vol. 1: 4p., Yunnan Science and Technology Press, China (2010).

Google translation of CN 102133351 (Year: 2011).

Chung "Neuroprotective Effect of a Chuk-Me-Sun-Dan on Neurons from Ischemic Damage and Neuronal Cell Toxicity" neurochem research 31(1):1-9 (Year: 2006).

Borten "chinese herbs" accessed from chineseherbinfo.com on Feb. 7, 2019 (Year: 2012).

Lee "Anti-inflammatory activity of the sclerotia of edible fungus poria cocos wolf and their active lanostane triterpenoids" j func food 32:27-36 (Year: 2017).

Healthline "mulberries 101: nutrition facts and health benefits" accessed from healthline.com on Jul. 11, 2019 (Year: 2019).

Machine translation of KR 20100070514, published Jun. 2010, received from STIC on Mar. 28, 2018 (Year: 2010).

Reitz C. Toward precision medicine in Alzheimer's disease. Ann Transl Med 2016;4(6}:107. (Year: 2016).

Stanford "Alzheimer's Prevention, Treatment and Research-A Q&A with Dr. Frank Longo" accessed from stanfordhealthcare.org (Year: 2016).

Wikipedia "wolfporia extensa" accessed from wikipedia.org (Year: 2018).

Google translation of KR 101251866 (Year: 2012).

European Extended Search Report dated Jan. 8, 2020, in European Patent Application No. EP19210811.6, Munich, Germany, 8 pages.

Rios, J-L, "Chemical Constituents and Pharmacological Properties of Poria cocos," Planta Med, 77 :681-691 (2011).

Rina, Rastakhina, "Health and Beauty with NSP," published online on Nov. 23, 2008, accessed at http://nsp-leader.blogspot.ru/2008/11/nsp.html, accessed on Jul. 5, 2018, (Russian language document), 5 pages.

Irina, Rastakhina, "Health and Beauty with NSP," published online on Nov. 23, 2008, accessed at http://nsp-leader.blogspot.ru/2008/11/nsp.html, accessed on Jul. 5, 2018, 4 pages.

International Search Report and Written Opinion for International Application No. PCT/KR2015/013134, ISA/KR, Daejeon, Republic of Korea, dated Oct. 20, 2016, 11 pages.

International Search Report and Written Opinion for International Application No. PCT/KR2015/013136, ISA/KR, Daejeon, Republic of Korea, dated May 25, 2016, 11 pages.

Shih, P-H., et al., "Antioxidant and cognitive promotion effects of anthocyanin-rich mulberry (*Morus atropurpurea* L.) on senescence-accelerated mice and prevention of alzheimer's disease," J. Nutro Biochem 21 (7): 598-605, (2010). Elsevier, Netherlands (2010).

Ya-long Feng, et al., "Chemical Constituents of Surface Layer of *Poria cocas* and their Pharmacological Properties (I)," China Journal of Chinese Materia Medicine, Zhongguo Zhongyao Zazhi, vol. 38, Issue 7, Apr. 2013.

\* cited by examiner

[Fig. 1]
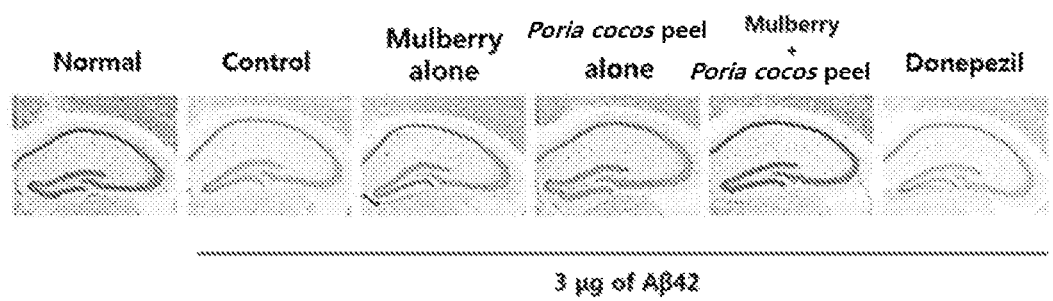
3 μg of Aβ42
[Fig. 2]
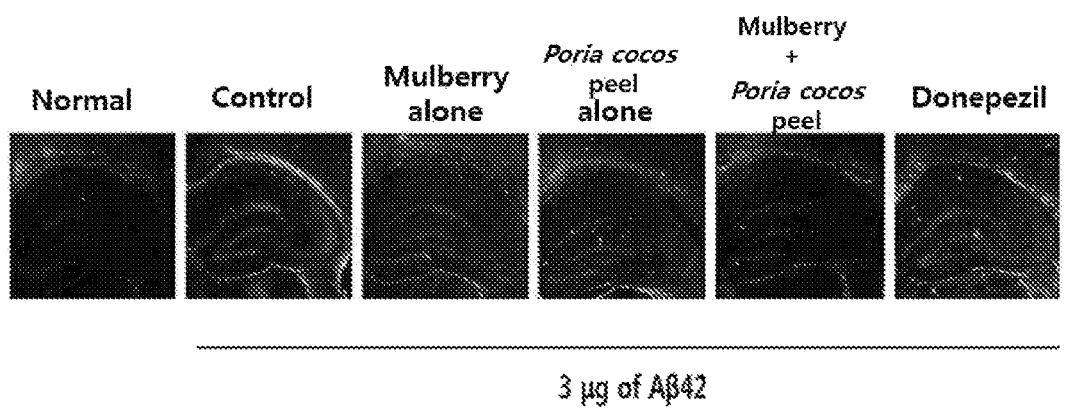
3 μg of Aβ42

COMPOSITION CONTAINING MIXED EXTRACT OF MULBERRY AND *PORIA COCOS* BARK FOR PREVENTING, IMPROVING OR TREATING NEURODEGENERATIVE DISORDERS

CROSS-REFERENCE TO RELATED APPLICATIONS

This patent application is a Continuation of U.S. patent application Ser. No. 15/535,489, filed on Jun. 13, 2017, which is a National Stage Entry of PCT/KR2015/013134, filed on Dec. 3, 2015, which claims priority to Korean Application 10-2014-0184854, filed on Dec. 19, 2014, each of which is hereby incorporated by reference in its entirety.

TECHNICAL FIELD

The present invention relates to a composition comprising the mixed extract of mulberry and *Poria cocos* peel for preventing, improving or treating neurodegenerative disorders.

RELATED ART

Degenerative neurological disease is a disease in which mental function is deteriorated due to gradual structural and functional loss of neurons. Degenerative neurologic disease may be accompanied by symptoms such as dementia, extrapyramidal abnormality, cerebellar abnormality, sensory disturbance, and movement disorder due to nerve cell degeneration in specific areas of the nervous system. In addition, complex symptoms may occur due to multiple abnormalities at the same time. The disease is diagnosed according to the clinical manifestation of the patient. However, the symptoms vary widely, and different diseases often have common clinical symptoms, making diagnosis be difficult (*Soc. Sci. Med*. Vol. 40. No. 6, pp. 847-858, 1995).

Degenerative neurological disease is a symptom of the disease slowly develops, and is often caused by aging. Once the disease has developed, the disease progresses continuously for several years or decades until death, and the fundamental treatment is difficult, so the social burden is great. It is known that genetic influences such as family history are very likely to be the cause of the disease, but acquired factors also play an important role. Degenerative neurological disorders can be classified according to their clinical symptoms, such as progressive dementia (Alzheimer's disease, etc.), neurological disorders (such as pick disease), posture and movement disorders (such as Parkinson's disease), progressive ataxia, muscular atrophy and weakness, sensory and motor disorders and so on (International Journal of Engineering and Technology, Vol. 2, No. 4, August 2010 Classification of Neurodegenerative Disorders Based on Major Risk Factors Employing Machine Learning Techniques).

Cytotoxicity of Aβ plaque and tangles of hyper-phosphorylated tau is attracting attention as a direct cause of Alzheimer's dementia, a typical degenerative brain disease.

Aβ is produced from the precursor APP and is produced by the action of enzymes such as β-secretase and γ-secretase, and is distributed outside the nerve cells. When the Aβ concentration is low, it is in a dissolved state, but when it is above a certain level, the Aβ proteins bind to each other to form an insoluble senile plaque. This substance can destroy peripheral nerve cells by causing inflammation and neurotoxicity. For example, neuronal death and microgranulosis observed in patients with Alzheimer's disease is thought to be associated with the senile plaque. In vitro test results showed that Aβ could induce activation of microglial cells (brain macrophages). This supports the hypothesis that microgranulosis and brain inflammation found in the brains of patients with Alzheimer's disease is a major cause of Aβ-induced Alzheimer's disease. To date, there have been no widely accepted therapies or therapies that are expected to remarkably dissolve Aβ once the senile plaque is formed, or to prevent the formation of deposits.

The tau consists of four parts: the N-terminal protruding part, the proline aggregation domain, the micro-organelle binding domain and the C-terminal (Mandelkow et al., Acta. Neuropathol., 103, 26-35, 1996). It plays a role in connecting the microtubules that form the physical structure of nerve cells. It is known that degenerative brain diseases such as tauopathy are caused by abnormally hyperphosphorylated or transformed tau in the nervous cells of the central nervous system Alzheimer's disease, Picks disease, Frontotemporal dementia and parkinsonism linked to chromosome 17(FTDP-17) and so on, are typical tauopathies (Lee et al., Annu. Rev. Neurosci., 24, 1121-1159, 2001; Bergeron et al., J. Neuropathol. Exp. Neurol., 56, 726-734, 1997; Bugiani et al., J. Neuropathol. Exp. Neurol., 58, 667-677, 1999; Delacourte et al., Ann. Neurol., 43, 193-204, 1998; Ittner and Gotz, Nat. Rev. Neurosci., 12, 65-72, 2011).

In the 1980s Alzheimer's study, neurotrophic factors were suggested to have therapeutic potential for degenerative neurological disorders (Nature. 1987 Sep. 3-9; 329(6134): 65-8. Amelioration of cholinergic neuron atrophy and spatial memory impairment in aged rats by nerve growth factor). Studies have shown that cholinergic neurons in the basal forebrain, lost due to aging, which is known to be one of the causes of Alzheimer's disease, are restored by administering nerve growth factor (NGF) to the lateral ventricle, resulting in an improvement in memory capacity of experimental animals. So, studies have been continuing to treat degenerative neurological diseases using neurotrophic factors. In a subsequent study, a study was carried out to restore motor nerve function by injecting Brain-derived neurotrophic factor (BDNF), Neurotrophin-3(NT-3), Neurotrophin-4(NT-4), and ciliary neurotrophic factor (CNTF), which are neurotrophic factor family into experimental animals that impaired motor nerve function by nodulating the facial nerve and sciatic nerve, and positive results were obtained (Nature. 1992 Dec. 24-31; 360(6406):757-9. Brain-derived neurotrophic factor prevents the death of motoneurons in newborn rats after nerve section.). Furthermore, in the experiment using a recombinant mouse (wobbler) with a disease in which the number and function of motor neurons were gradually lost as the aging progressed, the number of motor neurons was increased and the function was improved by administering BDNF and CNTF to the mouse (Science. 1994 Aug. 19; 265(5175):1107-10. Arrest of motor neuron disease in wobbler mice cotreated with CNTF and BDNF).

In addition, to the above-mentioned studies, it has been reported that neurotrophic factors improve memory, cognition, and behavioral disorders in experimental animals by increasing the number and function of neurons in various sensory and motor neuropathic models.

The scientific name of the mulberry is *Morus alba* (桑椹子), and when the fruit of the deciduous mulberry tree is magenta, it is picked, dried and used as a medicinal herb. In oriental medicine, it is known to be used for treating dizziness, tinnitus, thirsty and diabetes and so on. In Japan, it has the effect of treating Yanghyulguopoong and Wind-Heat, and is known to be applied to treatments such as tonic, pain medication, insomnia, tinnitus, dizziness, back pain, and constipation and so on (Namba, T., The Encyclopedia of Wakan-Yaku with Color Pictures Vol. 1 Hoikusha, Osaka, Japan, 1993). In Donguibogam, mulberry treats thirst and benefits five organs, and mulberry has mulberry tree's vital forces(精) (Donguibogam korean translation committee, Donguibogam, Namsandang, Seoul, Korea, 2000). In Chinese pharmacopoeia (CP), it is also prescribed medicines for the treatment of dizziness, tinnitus, insomnia and thirst etc.

Mulberry has anthocyanin, phenolic acid and flavonoid and so on, as main components and it has been reported that the isolated single component and its extract have blood glucose lowering, MAO (monoamine oxidase) inhibitory activity, antioxidative effect and neuronal cell protection effect.

The scientific name of Bokryeong (茯) is *Poria cocos*. *Poria cocos* is a plant of the class family Polyporaceae, in the order Aphyllophorales, in the class Eubasidiomycetes, Hymenomycetidae. *Poria cocos* is a kind of fungus belonging to *bacillus*, which is a brown rot fungus, which is a kind of saprophyte organism in the pine tree, but it is also parasitic to the root of living pine tree. Mycelium grows while branching to white, and hyphae start to grow together. When the proper environmental conditions such as temperature and humidity are continued, hard lumps of sclerotia are formed. This is called bokryeong. According to the color of the inside, white is *Poria cocos* wolf, rose pink is Jeokbokryeong. The outer shell of *Poria cocos* is called *Poria cocos* peel.

The main components of the *Poria cocos* are Parchymic acid ($C_{33}H_{52}O_5$), Pinicolic acid ($C_{30}H_{18}O_3$), 3β-Hydroxylanosta-7.9(11), 24-Trien-21-oic acid, Tumulosic acid ($C_{31}H_{50}O$), Ebricoic acid ($C_{31}H_{50}O_3$) and the like. It also contains purgiminic acid, ebricoic acid, Polypotenic acid A, C and triterpenoids etc. And it also contains ergosterol, lecithin, adenine, choline, glucose, fructose and protein, and a large amount of inorganic substances.

*Poria cocos* is sweet and the nature of *Poria cocos* is warm, and its taste and properties are all light, so it is said to be a medicinal substance with cool properties. In the past literature, it is described that the *Poria cocos* can relieve the thirst, discharge the urine smoothly, remove the moisture, moderate the body condition, and enhance energy by harmonizing the function of digestive system, by smoothing the waist, the circulation of abdominal blood eases well. It was mainly used for prescription related to memory. In recent articles, anti-diabetic and anticancer effects of *Poria cocos* have been reported (Ling Hui, Evaluation of the chemotherapeutic and chemopreventive potential of triterpenoids from *Poria cocos*, Ling Hui, doctoral thesis of department of pharmacy, National University of Singapore, 2010).

*Poria cocos* peel is the outer shell of *Poria cocos* sclerotium belonging to the polyporaceae. It is known as a medicinal substance that has the effect to moderate edema by releasing water. Especially, it contains abundantly lorostane-based triterpene poricoic acid, and Donguibogam states that the *Poria cocos* peel is used as a component of Opisan (tangerine peel, arrecae pericarpium, ginger peel, *morus alba* peel) prescribed for edema. In recent studies, it has been reported that *Poria cocos* peel have therapeutic effects such as diuretic, urinary stimulation, and edema reduction etc. (Triterpenes from the surface layer of *Poria cocos*, Takaaki tai, Phytochem, vol. 39, no. 5, 1995; Urinary metabonomic study of the surface layer of *Poria cocos* as an effective treatment for chronic renal injury in rats, ying yong zhao et al, Journal of Ethnopharmacology, vol. 148, no. 2, s2013).

With this background, the inventors have conducted studies to develop materials for pharmaceutical composition and food composition for the effective prevention, improvement and treatment of degenerative neurological diseases. As a result, the inventors of the present invention confirmed that these herbal extracts exhibit significant memory recovery activity in a brain neuropathy model induced by various brain injury or memory-inhibiting drugs during a neuropsychological activity study of the mulberry and *Poria cocos* peel. In addition, these herbal extracts have been shown to inhibit the production of substances that cause neuronal cell death in the brain and to protect the nerve cells by promoting the expression of proteins promoting neural cell regeneration and differentiation. The present inventors have completed the present invention by confirming that when the mulberry and *Poria cocos* peel herbal extracts are mixed at a certain ratio, they shows a maximum effect, compared to the herbal extract as a single component.

DETAILED DESCRIPTION OF THE INVENTION

Technical Problem

It is an object of the present invention to provide a pharmaceutical composition for preventing and treating of degenerative neurological diseases and a health functional food for preventing and ameliorating of degenerative neurological diseases, which contains a mixed extract of mulberry and *Poria cocos* peel as an active ingredient.

Technical Solution

In order to achieve the above object, the present invention provides a pharmaceutical composition for preventing and treating of degenerative neurological diseases, and a health functional food for preventing and ameliorating of degenerative neurological diseases, which are containing a mixed extract of mulberry and *Poria cocos* peel.

Advantageous Effect

According of the present invention, the mixed extract of mulberry and *Poria cocos* peel inhibits the production of amyloid-β (Abeta) and phosphorylation of tau which may cause degenerative brain diseases by inducing neuronal death, and exhibit an effect of protecting nerve cells by promoting the NGF production, which is a factor promoting a neural cell survival and differentiation. In addition, it exhibits an effect of inhibiting acetylcholine esterase (AChE) to increase nerve conduction and to mediate memory enhancing action. Therefore, the mixed extract of mulberry and *Poria cocos* peel can be effectively used for the development of pharmaceutical composition for preventing and treating of degenerative neurological diseases including dementia or for the development of health food for preventing and ameliorating of degenerative neurological diseases.

BRIEF DESCRIPTION OF DRAWINGS

FIG. 1 shows the results obtained by injecting a herbal mixed extract, a single extract, and a control drug in a model inducing neurotoxicity with beta amyloid, and staining with NeuN, a neural cell marker.

FIG. 2 shows the results obtained a mixed extract, a single extract, and a control drug to a model induced by neurotoxicity with beta amyloid, and staining with FJB, a cell death marker.

MODE OF THE INVENTION

Hereinafter, the present invention will be described in detail.

The present invention relates to a pharmaceutical composition for preventing or treating of degenerative neurological diseases, comprising a mixed extract of mulberry and *Poria cocos* peel as an active ingredient.

The mixed extract of the present invention can be provided according to a conventional method for preparing an herbal extract, but specifically means a crude extract obtained by using water, alcohol, or a mixture of water and alcohol. The alcohol which is one of the extraction solvents may be, but is not limited to, a lower alcohol having 1 to 4 carbon atoms, preferably methanol, ethanol, butanol or alcohol spirit, more preferably ethanol. Here, the alcohol spirit means ethanol produced by fermenting starch raw material or saccharide raw material and distilling it. Further, the mixed solvent of water and alcohol is not particularly limited, and may be mixed at any desired ratio.

In one embodiment of the present invention, the mixed extract of the mulberry and *Poria cocos* peel may be extracted with 60 to 80% (v/v) ethanol, 65 to 75 (v/v) % ethanol or 70 (v/v) %, but is not limited thereto.

In another embodiment of the present invention, the weight ratio of the mulberry and *Poria cocos* peel may be 4 to 7:1, 4 to 6:1 or 5:1, but is not limited thereto.

The mixed extract of the present invention includes all the forms of an extract obtained by extracting a mixture of mulberry and *Poria cocos* and an extract obtained by separately extracting mulberry and *Poria cocos* separately and then mixing each extract. Specifically, mulberry and *Poria cocos* peel are mixed and extracted at the weight ratio, or mulberry and *Poria cocos* peel are respectively extracted by appropriate methods, and then each extract is mixed at the weight ratio.

More specifically, the mixed extract of the present invention can be obtained as follows. First, the mulberry and *Poria cocos* peel are washed and dried, respectively, and then the dried herbs are cut to obtain the cut herbs. The dried cut of mulberry and *Poria cocos* peel are mixed at a weight ratio of 0.1 to 10 times as the weight of the *Poria cocos* peel, and preferably, the mixture is prepared by mixing at a weight ratio of mulberry:*Poria cocos* peel=4 to 7:1. Water, lower alcohol having 1 to 4 carbon atoms or a mixture of water and the lower alcohol, preferably 70(v/v) % ethanol, is added to the mixture of mulberry and *Poria cocos* peel in an amount of 1 to 20(v/w) times, or preferably 5 to 10(v/w) times as the weight of the mixture. Then, the mixture is subjected to extraction at a temperature of 10° C. to 100° C., preferably at room temperature for 1 hour to 72 hours, preferably 48 hours according to cold water extraction, hot water extraction, ultrasonic extraction, reflux cooling extraction, heat extraction, or supercritical extraction. Preferably, the extraction can be performed by cold water extraction once, and concentration under reduced pressure to produce a mixed extract of mulberry and *Poria cocos* peel.

The composition containing the mixed extract of mulberry and *Poria cocos* peel according to the present invention as an active ingredient can be used for the treatment of degenerative neurological diseases. Accordingly, the present invention provides a pharmaceutical composition for preventing and treating degenerative neurological diseases, which comprises a mixed extract of mulberry and *Poria cocos* peel as an active ingredient and an use of a mixed extract of mulberry and *Poria cocos* peel for the preparation of a therapeutic agent for degenerative neurological diseases, and a method of treating a degenerative neurological disease comprising administering to a subject a therapeutically effective amount of the mixed extract of a mulberry and *Poria cocos* peel.

As described above, the degenerative neurological disease according to the present invention means a degenerative disease of mental function caused by gradual structural and functional loss of nerve cells (neurons). Specifically, it includes diseases selected from the group consisting of Alzheimer's disease, Creutzfeldt-Jakob disease, Huntington's disease, multiple sclerosis, Guilin-Barre syndrome, Parkinson's disease, Lou Gehrig's disease, progressive dementia caused by gradual neuronal death and progressive ataxia and so on.

In one embodiment of the present invention, the pharmaceutical composition for preventing and treating of degenerative neurological diseases containing the mixed extract of mulberry and *Poria cocos* peel as an active ingredient at an amount of 0.01 to 90 parts by weight, 0.1 to 90 parts by weight, 1 to 90 parts by weight, or 10 to 90 parts by weight, based on 100 parts by weight of the total pharmaceutical composition, but is not limited thereto, and may vary depending on the condition and the type and progress of disease.

In another embodiment of the present invention, the pharmaceutical composition for preventing and treating degenerative neurological diseases containing the mixed extract of mulberry and *Poria cocos* peel as an active ingredient may be formulated into pharmaceutical preparations for the prevention and treatment of degenerative neurological disorders, including pharmaceutically acceptable carriers, diluents or excipients.

Examples of the carrier, excipient and diluent include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil.

The composition of the present invention may be formulated in the form of oral preparations such as powders, granules, tablets, capsules, suspensions, emulsions, syrups, aerosols and a form of external preparation, suppository or sterilized injection solution in accordance with a conventional method in order to prepare them in the form of medicines. In general, in the case of formulation, it can be prepared by using a diluent such as filler, an extender, a binder, a wetting agent, a disintegrant, a surfactant, or an excipient which is usually used. Solid form preparations for oral administration include tablets, pills, powders, granules, capsules and the like, which may contain at least one excipient such as starch, calcium carbonate, sucrose, lactose, gelatin and the like. In addition to simple excipients, lubricants such as magnesium stearate and talc may also be used. Liquid preparations for oral use include suspensions, solutions, emulsions, and syrups. In addition to commonly used simple diluents such as water and liquid paraffin, various excipients such as humectants, sweeteners, fragrances, preservatives and the like may be included. Formulations for parenteral administration include sterilized aqueous solutions, non-aqueous solutions, suspensions, emulsions, freeze-dried preparations and suppositories. Examples of the suspending agent include propylene glycol, polyethylene glycol, vegetable oil such as olive oil, injectable ester such as ethyl oleate, and the like. Examples of the suppository base include witepsol, macrogol, tween 61, cacao butter, laurinum, and glycerogelatin and so on.

The present invention provides a method for treating a neurodegenerative disease, which comprises administering a pharmaceutical composition containing the mixed extract of the mulberry and *Poria cocos* peel as an active ingredient to a mammal, including a human, in a therapeutically effective amount.

The dosage of the pharmaceutical composition for the prevention and treatment of degenerative neurological diseases containing the mixed extract of mulberry and *Poria cocos* peel as an active ingredient of the present invention may vary depending on the age, sex, and body weight of the patient, Generally, an amount of 0.1 to 100 mg/kg, preferably 1 to 30 mg/kg, may be administered once to several times per day. The dosage may also be increased or decreased depending on the route of administration, degree of disease, sex, body weight, age, health condition, diet, administration time, administration method, excretion rate and the like. Accordingly, the dose is not intended to limit the scope of the invention in any way.

The pharmaceutical composition containing the mixed extract of mulberry and *Poria cocos* peel of the present invention can be administered in various routes to mammals such as rats, mice, livestock, and humans. All modes of administration may be expected, for example, by oral, rectal or intravenous, intramuscular, subcutaneous, intra-uterine dural or intracerebral injection.

The mixed extract of mulberry and *Poria cocos* peel in accordance with the present invention has little toxicity and side effects, and therefore can be safely used for long-term use for preventive purposes.

The present invention also provides a food composition comprising the mixed extract of mulberry and *Poria cocos* peel. The mixed extract of mulberry and *Poria cocos* peel inhibits the production of substances causing neuronal cell death in the brain and promote the expression of proteins promoting neural cell regeneration and differentiation to protect nerve cells and can be effectively used for the production of health functional food and general food which can exhibit the effect of preventing and improving neurodegenerative diseases in particular.

Specifically, the health functional food defined in the present invention is defined by the "Act on Health Functional Foods 2002" newly defined as "the functional and safety of the human body has been sufficiently established and the Food and Drug Administration Notice 2004-12 Of the Regulation on the Recognition of Ingredients of Health Functional Foods or Ingredients prescribed in the Act".

The food composition containing the mixed extract of mulberry and *Poria cocos* peel according to the present invention can be used variously for food for symptom relief of degenerative neurological diseases. As a food to which the herbal extract of the present invention can be added, various foods such as beverages, gums, tea, vitamin complex, health functional food, and health functional beverage and they can be used in the form of pills, powders, granules, infusions, tablets, capsules or beverages.

The amount of the mixed extract of mulberry and *Poria cocos* peel in the food of the present invention is generally 0.1 to 15% by weight, preferably 0.2 to 10 wt %, and in the case of the health functional beverage composition, 0.1 to 30 g, preferably 0.2 to 5 g, based on 100 ml, may be included.

When the food composition according to the present invention is prepared in a beverage form, there are no particular restrictions on the liquid ingredients other than those containing the herbal extracts as essential ingredients in the proportions indicated. In addition, various flavoring agents or natural carbohydrates may be added as an additional ingredient, such as ordinary beverages.

Examples of the above-mentioned natural carbohydrates include monosaccharides such as glucose and fructose; Disaccharides such as maltose, sucrose; Polysaccharides such as Dextrin, cyclodextrin and the like, or sugar alcohols such as xylitol, sorbitol and erythritol and so on. As natural flavors other than those mentioned above, natural flavoring agents (thaumatin, stevia extract (e.g., rebaudioside A, glycyrrhizin etc.)) and synthetic flavors (saccharin, aspartame, etc.) can be advantageously used. The ratio of the natural carbohydrate is generally about 1 to 20 g, preferably about 5 to 12 g per 100 ml of the total composition of the present invention.

In addition to the above, the food composition of the present invention may further contain various additives such as various nutrients, vitamins, minerals (electrolytes), flavorings such as synthetic flavors and natural flavors, colorants and thickeners, pectic acid and its salts, alginic acid and its salts, organic acids, protective colloid thickeners, pH adjusting agents, stabilizers, preservatives, glycerin, alcohols, carbonating agents used in carbonated drinks, and the like. In addition, the compositions of the present invention may contain natural fruit juice and pulp for the production of fruit juice drinks and vegetable drinks. These components can be used independently or in combination. The ratio of such additives is not particularly limited, but is generally selected in the range of 0 to about 20 parts by weight per 100 parts by weight of the total food composition of the present invention. In another embodiment, the present invention is a method for preventing, ameliorating or treating a degenerative neurological disease, comprising administering a composition containing an active ingredient of a combination of the mixed extract of mulberry and *Poria cocos* peel. Alternatively, the present invention provides a use of the mixed extract of mulberry and *Poria cocos* peel for preventing, ameliorating or treating a degenerative neurological disease. The dose, dosage form, administration method, etc. of the composition containing mulberry and *Poria cocos* peel mixed extract for such method or use are as mentioned above.

DETAILED DESCRIPTION OF THE INVENTION

The present invention will be explained in detail with reference to the following examples and experiments. However, the following examples and experiments are only to illustrate the present invention, and the scope of the present invention is not limited thereto.

<Example 1> Preparation of *Poria cocos* Peel Extract According to the Present Invention Dried mulberry and *Poria cocos* peel were purchased on herbal medical store in Kyungdong market and contaminants were removed and well-dried herbal was used for the experiment. Mulberry and *Poria cocos* peel cut with a cutting machine were mixed at a weight ratio of 5:1 in an amount of 300 g. And 3 L of 70 (v/v) % aqueous ethanol solution was added to the herbal mixture and the mixture was cooled at room temperature for 48 hours. After filtration, the mixture was concentrated under reduced pressure, and then lyophilized to obtain a crude herbal extract (crude extract) to give Example 1 (See Table 1).

TABLE 1

Preparation of *Poria cocos* peel extract according to the present invention

| Preparation of *poria cocos* peel extract according to the present invention | Raw material amount (g) | | Solvent selection | Amount of solvent | Extraction temperature | Extraction time | Product (g) | Yield (%) |
|---|---|---|---|---|---|---|---|---|
| | Mulberry | *Poria cocos* peel | | | | | | |
| Example 1 | 250 | 50 | 70% EtOH | 3 L | Room temperature | 2 days | 19.75 | 6.58 |

<Comparative Example 1> Preparation of Mulberry Extract 200 g of the same botanical raw material mulberry as Example 1 was prepared according to the same method of Example 1 to obtain a crude extract of Mulberry, which was used as Comparative Example 1 (See Table 2).

<Comparative Example 2> Preparation of *Poria cocos* Peel Extract 200 g of the same botanical raw material of *Poria cocos* peel as Example 1 was prepared according to the same method of Example 1 to obtain a crude extract of *Poria cocos* peel as Comparative Example 2 (see Table 2).

TABLE 2

Yield of single extracts of mulberry and *Poria cocos* peel

| | Raw material amount (g) | | Solvent type | Solvent amount | Extraction temperature | Extraction time | Product (g) | Yield (%) |
|---|---|---|---|---|---|---|---|---|
| | Mulberry | *Poria cocos* peel | | | | | | |
| Comparative Example 1 | 200 | — | 70% EtOH | 2 L | Room temperature | 2 days | 8.4 | 4.2 |
| Comparative Example 2 | — | 200 | 70% EtOH | 2 L | Room temperature | 2 days | 6.8 | 3.4 |

<Comparative Examples 3 to 8> Preparation of Mixed Crude Extracts of Mulberry and *Poria cocos* Peel The same botanical raw material as the mulberry and *Poria cocos* peel used in Example 1 was used in the experiment. Mulberry and *Poria cocos* peel cut with a cutting machine, Mulberry and *Poria cocos* peel were mixed as shown in Table 3, and then 70% ethanol aqueous solution having a volume of 10 times of the herbal mixture volume was added to the herbal mixture, and the mixture was cold-extracted at room temperature for 48 hours, After concentration under reduced pressure, the mixture was lyophilized to obtain a crude herbal extract (crude extract), which was used as Comparative Examples 3 to 8.

TABLE 3

Yield of mixed herbal extracts of mulberry and *Poria cocos* peel

| | Raw material amount (g) | | Solvent selection | Amount of solvent | Extraction temperature | Extraction time | Product (g) | Yield (%) |
|---|---|---|---|---|---|---|---|---|
| | Mulberry | *Poria cocos* peel | | | | | | |
| Comparative Example 3 | 100 | 100 | 70% EtOH | 2 L | Room temperature | 2 days | 16.96 | 8.48 |
| Comparative Example 4 | 150 | 50 | 70% EtOH | 2 L | Room temperature | 2 days | 15.78 | 7.89 |

TABLE 3-continued

Yield of mixed herbal extracts of mulberry and *Poria cocos* peel

| | Raw material amount (g) | | Solvent selection | Amount of solvent | Extraction temperature | Extraction time | Product (g) | Yield (%) |
|---|---|---|---|---|---|---|---|---|
| | Mulberry | *Poria cocos* peel | | | | | | |
| Comparative Example 5 | 200 | 20 | 70% EtOH | 2.2 L | Room temperature | 2 days | 14.39 | 6.54 |
| Comparative Example 6 | 50 | 150 | 70% EtOH | 2 L | Room temperature | 2 days | 14.20 | 7.10 |
| Comparative Example 7 | 40 | 200 | 70% EtOH | 2.4 L | Room temperature | 2 days | 18.94 | 7.89 |
| Comparative Example 8 | 20 | 200 | 70% EtOH | 2.2 L | Room temperature | 2 days | 19.76 | 8.98 |

<Experimental Example 1> Test of Memory Improvement and Nerve Cell Protection Effect of the Mixed Herb Extracts <1-1> Preparation of Experimental Animals Scopolamine Induced Memory Impairment Model Six-week-old ICR mice were used for the experiment and each experimental group consisted of 8 animals.

After 30 minutes of the Conducting drug (Example), Comparative drug (comparative example) and Donepezil (Control drug) oral administration, 1 mg/kg scopolamine was intraperitoneally administered. Normal animals were injected with the same amount of physiological saline. Behavioral studies were performed after 30 minutes of scopolamine administration.

Aβ Infusion Model

Six-week-old ICR mice were used in the experiment. The animals were anesthetized, fixed in a stereotaxic apparatus (Stoelting) and injected with 3 μl of vehicle (artificial CSF) or $Aβ_{42}$ for 6 minutes using a Hamilton micro syringe (fitted with a 26-gauge needle).

Animals treated with $Aβ_{42}$ were randomly divided into experimental groups. From 2 days after administration of $Aβ_{42}$, the experimental drug and the positive control drug were administered once a day for 11 days.

The lyophilized drug, comparative drug and control drug were suspended in 3% HPMC aqueous solution, and all the drugs were prepared on the day of the experiment.

Measurement of Protein in Brain

To examine the efficacy of mixed herbal extracts on the production of nerve cell death inducer or substances involved in cell protection, Six weeks old ICR mouse were administered the experimental drug, the comparative drug and the control drug for 5 days. On the 5th day 4 hours after the administration, Experimental animals were sacrificed and the brain was separated. Parts except cerebellum and Medulla oblongata were used in the experiment.

<1-2> Passive Avoidance Task

Passive avoidance experiments were performed in two independently separated bright and dark square boxes. Bright areas (20×20×20 cm) were illuminated with 50 W incandescent lamps. Light and dark areas (20×20×20 cm) were spaced 1 cm apart and 2 mm stainless steel rods were installed.

In the habituation phase, the two sections were separated by a guillotine door (5×5 cm), and the guillotine door was opened after 30 seconds after placing the experimental animals in the light section. The animals were allowed to freely navigate. When they reached the dark area, the guillotine door was closed and the animals were taken out after 3 seconds.

Acquisition trials were conducted 24 hours later. After 30 minutes of drug administration, 1 mg/kg of scopolamine was intraperitoneally administered and 30 minutes later, the behavioral experiment was performed. The experimental mice were initially placed in the bright zone and the door between the zones was opened after 30 seconds. When the experimental mice entered the dark area, the guillotine door was closed, and an electrical foot shock was immediately applied through a stainless steel rod for 2 seconds at 0.5 mA intensity, and the animals were taken out after 10 seconds. The time that the animals entered the dark zone was measured.

After performing the acquisition trials and giving a 24-hour rest period, the experimental animals were placed in a bright area for measuring the retention trial and the time until entering the dark area was measured. Both the acquisition trial and the retention trial were performed to determine the time taken for the mouse to enter all four feet in a dark room from a bright room.

As a result, as shown in Tables 4 and 5 below, the memory improvement effect was confirmed in each of the memory loss model by scopolamine and the $Aβ_{42}$-induced Alzheimer's dementia induction model. Compared with Comparative Examples 1 and 2, which are sole extracts of mulberry and *Poria cocos* peel, and Comparative Examples 3 to 8, which are mixed extracts of mulberry and *Poria cocos* peel, mulberry, *Poria cocos* peel 5:1 mixture showed significant spatial memory enhancement effect. The mixed extract of Example 1 showed an efficacy equal to or higher than 1 mg/kg of donepezil (DPZ), which is known as an acetylcholinesterase inhibitor.

TABLE 4

Scopolamine model - memory enhancing efficacy in passive avoidance experiment

| | Raw material amount (g) | | Total weight comparison Mulberry: *Poria cocos* peel weight ratio | Volume (mg/kg) | Acquisition time | Retention time |
|---|---|---|---|---|---|---|
| | Mulberry | *Poria cocos* peel | | | | |
| Normal | | | | | 62.8 | 270.3 |
| Vehicle | | | | | 72.3 | 92.3 |

TABLE 4-continued

Scopolamine model - memory enhancing efficacy in passive avoidance experiment

| | Raw material amount (g) | | Total weight comparison Mulberry: | | | |
|---|---|---|---|---|---|---|
| | Mulberry | Poria cocos peel | Poria cocos peel weight ratio | Volume (mg/kg) | Acquisition time | Retention time |
| example 1 | 250 | 50 | 5:1 | 100 | 59.4 | 255.9 |
| Comparative Example 1 | 200 | — | Mulberry alone | 100 | 88.8 | 110.4 |
| Comparative Example 2 | — | 200 | Poria cocos peel alone | 100 | 77.5 | 187.2 |
| Comparative Example 3 | 100 | 100 | 1:1 | 100 | 69.3 | 163.2 |
| Comparative Example 4 | 150 | 50 | 3:1 | 100 | 64.2 | 189.9 |
| Comparative Example 5 | 200 | 20 | 10:1 | 100 | 58.7 | 172.8 |
| Comparative Example 6 | 50 | 150 | 1:3 | 100 | 66.1 | 151.8 |
| Comparative Example 7 | 40 | 200 | 1:5 | 100 | 83.4 | 157.3 |
| Comparative Example 8 | 20 | 200 | 1:10 | 100 | 59.2 | 168.6 |
| Donepezil | | | | 1 | 77.4 | 243.5 |

TABLE 5

$A\beta_{42}$ administration model - memory enhancing efficacy in passive avoidance experiment

| | Raw material amount (kg) | | Total weight comparison Mulberry: | | | |
|---|---|---|---|---|---|---|
| | Mulberry | Poria cocos peel | Poria cocos peel weight ratio | Volume (mg/kg) | Acquisition time | Retention time |
| Normal | | | | | 52.4 | 285.3 |
| Vehicle | | | | | 66.9 | 99.9 |
| example 1 | 250 | 50 | 5:1 | 100 | 71.3 | 269.7 |
| Comparative Example 1 | 200 | — | Mulberry alone | 100 | 49.8 | 152.4 |
| Comparative Example 2 | — | 200 | Poria cocos peel alone | 100 | 41.2 | 138.9 |
| Comparative Example 3 | 100 | 100 | 1:1 | 100 | 39.8 | 163.2 |
| Comparative Example 4 | 150 | 50 | 3:1 | 100 | 57.4 | 188.9 |
| Comparative Example 5 | 200 | 20 | 10:1 | 100 | 62.5 | 162.2 |
| Comparative Example 6 | 50 | 150 | 1:3 | 100 | 51.3 | 143.1 |
| Comparative Example 7 | 40 | 200 | 1:5 | 100 | 46.9 | 127.6 |
| Comparative Example 8 | 20 | 200 | 1:10 | 100 | 38.6 | 142.9 |
| Donepezil | | | | 1 | 78.4 | 244.2 |

<1-3> Y-Maze Test

The Y-maze experiment was conducted to investigate the effect of short-term memory. The animals were placed on one arm of the Y-maze and allowed to move freely for 8 minutes. Spontaneous alternation and total number of entries were measured. When the animals were consecutively entered into three arms, they were defined as alternation entry, and the ratio was calculated by the following equation 1.

$$\text{Spontaneous alternation ratio (\%)} = [(\text{number of changes})/(\text{total number of arm entry}-2)] \times 100 \quad \text{[Equation 1]}$$

As a result, as shown in Tables 6 and 7, we confirmed the memory improvement effect in the memory decline model by scopolamine and $A\beta_{42}$-induced Alzheimer's dementia induction model. Particularly, in comparison with Comparative Examples 1 and 2, which are the sole extracts of mulberry and Poria cocos peel, and Comparative Examples 3 to 8, which are mixed extracts of mulberry and Poria cocos peel, 5:1 mixture of mulberry and Poria cocos peel according to Example 1 showed significant cognitive and memory enhancing effect. In particular, the mixed extract of Example 1 showed better efficacy than Donepezil (DPZ) 1 mg/kg, which is known as the acetyl cholinesterase inhibitor.

TABLE 6

Scopolamine model - memory-enhancing efficacy in Y-maze experiment

| | Raw material amount (kg) | | Total weight comparison Mulberry: | | | | |
|---|---|---|---|---|---|---|---|
| | Mulberry | Poria cocos peel | Poria cocos peel weight ratio | Volume (mg/kg) | Total number of entries | True enter | spontaneous alternation (%) |
| Normal | | | | | 42 | 32 | 76.2 |
| Vehicle | | | | | 51 | 27 | 52.9 |
| example 1 | 250 | 50 | 5:1 | 100 | 50 | 36 | 72.0 |
| Comparative Example 1 | 200 | — | Mulberry alone | 100 | 40 | 23 | 57.5 |
| Comparative Example 2 | — | 200 | Poria cocos peel alone | 100 | 41 | 26 | 63.4 |
| Comparative Example 3 | 100 | 100 | 1:1 | 100 | 48 | 29 | 60.4 |

TABLE 6-continued

Scopolamine model - memory-enhancing efficacy in Y-maze experiment

| | Raw material amount (kg) | | Total weight comparison Mulberry: Poria cocos peel weight ratio | Volume (mg/kg) | Total number of entries | True enter | spontaneous alternation (%) |
|---|---|---|---|---|---|---|---|
| | Mulberry | Poria cocos peel | | | | | |
| Comparative Example 4 | 150 | 50 | 3:1 | 100 | 35 | 23 | 65.7 |
| Comparative Example 5 | 200 | 20 | 10:1 | 100 | 40 | 25 | 62.5 |
| Comparative Example 6 | 50 | 150 | 1:3 | 100 | 33 | 19 | 57.6 |
| Comparative Example 7 | 40 | 200 | 1:5 | 100 | 59 | 33 | 55.9 |
| Comparative Example 8 | 20 | 200 | 1:10 | 100 | 42 | 27 | 64.3 |
| Donepezil | | | | 1 | 64 | 43 | 67.2 |

TABLE 7

$A\beta_{42}$ administration model - memory enhancing efficacy in Y-maze experiment

| | Raw material amount (kg) | | Total weight comparison Mulberry: Poria cocas peel weight ratio | Volume (mg/kg) | Total number of entries | True enter | spontaneous alternation (%) |
|---|---|---|---|---|---|---|---|
| | Mulberry | Poria cocas peel | | | | | |
| Normal | — | — | — | — | 37 | 29 | 78.4 |
| Vehicle | — | — | — | — | 38 | 19 | 50.0 |
| example 1 | 250 | 50 | 5:1 | 100 | 59 | 45 | 76.3 |
| Comparative Example 1 | 200 | — | Mulberry alone | 100 | 45 | 28 | 62.2 |
| Comparative Example 2 | — | 200 | Poria cocos peel alone | 100 | 42 | 28 | 66.7 |
| Comparative Example 3 | 100 | 100 | 1:1 | 100 | 36 | 22 | 61.1 |
| Comparative Example 4 | 150 | 50 | 3:1 | 100 | 51 | 35 | 68.6 |
| Comparative Example 5 | 200 | 20 | 10:1 | 100 | 42 | 25 | 59.5 |
| Comparative Example 6 | 50 | 150 | 1:3 | 100 | 33 | 20 | 60.6 |
| Comparative Example 7 | 40 | 200 | 1:5 | 100 | 58 | 35 | 60.3 |
| Comparative Example 8 | 20 | 200 | 1:10 | 100 | 44 | 24 | 54.5 |
| Donepezil | — | — | — | 1 | 61 | 43 | 70.5 |

<1-4> Novel Object Recognition (NOR) Task

Inside a black box of 45 cm width, 45 cm length, 50 cm height, two plastic objects of the same size but different shapes were placed. The experimental animals were allowed to move freely for 8 minutes and the time spent on each object was measured (training session) 24 hours later, the experimental animals were placed in a box with one familiar object and one new object in the training session and the time spent in each object was measured (test session). The recorded values were calculated using the following equation (2), which is expressed as a recognition result of a new object.

Recognition rate of new objects (%)=Time spent on new objects/(Time spent on new objects+Time spent on experienced objects)×100  [Equation 2]

As a result, as shown in Tables 8 and 9, we confirmed the memory improvement effect in the each of the scopolamine-induced memory decline models and the $A\beta_{42}$-induced Alzheimer's models. Compared with Comparative Examples 1 and 2, which are sole extracts of mulberry and Poria cocos peel, and Comparative Examples 3 to 8, which are mixed extracts of mulberry and Poria cocos peel, mulberry, Poria cocos peel 5:1 mixture showed significant cognitive and memory enhancement. Compared with Donepezil (DPZ) 1 mg/kg, which is known as the acetyl cholinesterase inhibitor, the mixed extract of Example 1 showed the equivalent cognitive and memory improving effect in the scopolamine induced memory formation inhibition model, and exhibited a cognitive and memory improvement effect equal to or higher than that of the $A\beta_{42}$ administration model.

TABLE 8

Scopolamine Model - Memory Enhancement Effect in NOR Experiment

| | Raw material amount (kg) | | Total weight comparison Mulberry: Poria cocos peel weight ratio | Volume (mg/kg) | New object recognition time | Familiar object recognition time | Total object recognition time | New object recognition time ratio (%) |
|---|---|---|---|---|---|---|---|---|
| | Mulberry | Poria cocas peel | | | | | | |
| Normal | — | — | — | — | 13.7 | 5.3 | 19.0 | 72.1 |
| Vehicle | — | — | — | — | 11.6 | 13.9 | 25.5 | 45.5 |
| example 1 | 250 | 50 | 5:1 | 100 | 7.4 | 3.9 | 11.3 | 70.2 |
| Comparative Example 1 | 200 | — | Mulberry | 100 | 3.8 | 5.6 | 9.4 | 50.4 |
| Comparative Example 2 | — | 200 | Poria cocos peel | 100 | 11.2 | 8.3 | 19.5 | 64.2 |
| Comparative Example 3 | 100 | 100 | 1:1 | 100 | 16.6 | 12.7 | 29.3 | 56.7 |
| Comparative Example 4 | 150 | 50 | 3:1 | 100 | 12.3 | 11.6 | 23.9 | 61.5 |
| Comparative Example 5 | 200 | 20 | 10:1 | 100 | 11.3 | 12.3 | 23.6 | 57.9 |
| Comparative Example 6 | 50 | 150 | 1:3 | 100 | 13.0 | 11.5 | 24.5 | 53.1 |
| Comparative Example 7 | 40 | 200 | 1:5 | 100 | 11.1 | 9.8 | 20.9 | 57.1 |
| Comparative Example 8 | 20 | 200 | 1:10 | 100 | 15.3 | 13.9 | 29.2 | 61.4 |
| Donepezil | — | — | — | 1 | 12.9 | 7.9 | 20.8 | 68.0 |

TABLE 9

$A\beta_{42}$ administration model - memory enhancing efficacy in NOR experiment

| | Raw material amount (kg) | | Total weight comparison Mulberry: Poria cocos peel weight ratio | Volume (mg/kg) | New object recognition on time | New object recognition on time | Total object recognition on time | New object recognition on time ratio (%) |
|---|---|---|---|---|---|---|---|---|
| | Mulberry | Poria cocas peel | | | | | | |
| Normal | — | — | — | — | 19.7 | 5.3 | 25.0 | 78.8 |
| Vehicle | — | — | — | — | 12.6 | 13.9 | 26.5 | 47.5 |
| example 1 | 250 | 50 | 5:1 | 100 | 13.4 | 3.9 | 17.3 | 77.5 |
| Comparative Example 1 | 200 | — | Mulberry | 100 | 9.8 | 5.6 | 15.4 | 63.6 |
| Comparative Example 2 | — | 200 | Poria cocos peel | 100 | 17.2 | 8.3 | 25.5 | 67.5 |
| Comparative Example 3 | 100 | 100 | 1:1 | 100 | 22.6 | 12.7 | 35.3 | 64.0 |
| Comparative Example 4 | 150 | 50 | 3:1 | 100 | 18.3 | 11.6 | 29.9 | 61.2 |
| Comparative Example 5 | 200 | 20 | 10:1 | 100 | 14.3 | 12.3 | 26.6 | 53.8 |
| Comparative Example 6 | 50 | 150 | 1:3 | 100 | 16.0 | 11.5 | 27.5 | 58.2 |
| Comparative Example 7 | 40 | 200 | 1:5 | 100 | 17.1 | 9.8 | 26.9 | 63.6 |
| Comparative Example 8 | 20 | 200 | 1:10 | 100 | 21.3 | 13.9 | 35.2 | 60.5 |
| Donepezil | — | — | — | 1 | 18.9 | 7.9 | 26.8 | 70.5 |

<1-5> Immunohistochemical Staining

For immunohistochemical staining, the Aβ infusion animal described in Experimental Example 1-1 was perfused with 1×PBS (phosphate buffered saline), fixed with 4% paraformaldehyde, and brain was extracted. This was fixed in the same solution for one day and stored in a 30% sucrose solution and the solution was changed every two days until frozen at 4° C. After that, brain tissue was frozen sufficiently at −20° C. by dropping OCT (optimal cutting temperature) compound in a cryostat, and then made into a 30 μm-thick section, and stored at 4° C. in a preservative solution. Immunohistochemical staining was performed with the hippocampus portion. The tissues washed with PBS were treated with 1% $H_2O_2$ for 15 minutes, After that the tissues were treated with 0.05 M PBS, 1.5% normal goat serum, 0.5 mg/ml bovine serum albumin, 0.3% triton X-100 and goat NeuN primary antibody (1:500) and were reacted at 4° C. for 24 hours to prevent nonspecific reactions. After the primary antibody was removed, the tissue was reacted with a peroxidase-conjugated secondary antibody (1:200) for 90 minutes, and the ABC was diluted in the buffer and allowed to react at room temperature for about 1 hour. After washing three times with PBS, the tissue was developed with 0.02% DAB and 0.01% $H_2O_2$ and subjected to ethanol and xylene dehydration to prepare slide samples.

For FJB (Fluoro-Jade-B) staining, tissue sections were fixed with PBS containing 4% paraformaldehyde for 5 minutes and stored at −70° C. The next day, the slides dried for 3 hours were immersed in a 0.06% permanganate potassium nitrate solution for 10 minutes. After rinsing with water, the slides were soaked in 0.1% acetic acid and 0.0004% FJB solution (Calbiochem, San Diego, Calif., USA) for 20 minutes. The slides were washed three times with distilled water and dried at 55° C. for 10 minutes. A multifocal microscope (Olympus, Japan) was used for imaging and the photographs were taken with a soft imaging system video camera.

As a result, as shown in FIG. 1, NeuN expression as a marker of neuron cells was higher than that of the control group by administration of mixed extract of botanical raw materials. This means that the reduction of neuronal cells was suppressed in the herbal mixed extract administration group. The extracts of mulberry and *Poria cocos* peel alone had a protective effect on neurons but were weaker in efficacy than herbal mixed extracts. Donepezil, the control drug, failed to show neuroprotective effects.

As shown in FIG. 2, the expression of FJB, a marker of apoptosis, was decreased by the herbal mixed extract as compared with the control. This result implies that the increase in the number of nerve cells identified in FIG. 1 is mediated through inhibition of neuronal cell death induced by aggregation of beta amyloids.

<1-6> Measurement of Beta Amyloid Production in Brain

ELISA experiments were conducted to investigate the inhibitory effect of herbal mixed extracts on beta amyloid production, which is known to be a major cause of Alzheimer's disease.

The brain of normal animals in Experimental Example <1-1> was extracted, and then the hippocampal region was separated, and RIPA buffer was added and homogenized mechanically. After centrifugation, the supernatant was taken and beta amyloid (IBL) concentration was measured. The amount of $A\beta_{40}$ expression in 1 mg protein was measured.

As a result, as shown in the following Table 10, it was confirmed that the production of beta amyloid was remarkably decreased by administration of the herbal mixed extract. Compared with Comparative Examples 1 and 2, which are sole extracts of mulberry and *Poria cocos* peel, and Comparative Examples 3 to 8, which are mixed extracts of mulberry and *Poria cocos* peel, mulberry and *Poria cocos* peel 5:1 mixture showed a higher inhibitory effect on beta amyloid formation. Single herbal extracts also showed beta amyloid-reducing activity. Among them, mulberry extract showed a relatively strong inhibitory effect on β-amyloid formation, and beta-amyloid-reducing effect was increased in mixed extract of botanical raw materials when the weight ratio of mulberry was high.

Donepezil (DPZ), an acetyl cholinesterase inhibitor used in Alzheimer's disease, did not affect beta amyloid production at a dose of 1 mg/kg.

TABLE 10

Normal animal model - $A\beta_{40}$ measurement

| | Raw material amount (kg) | | Total weight comparison Mulberry:*Poria cocos* peel weight ratio | Volume (mg/kg) | $A\beta_{40}$ concentration (pg/mg) |
|---|---|---|---|---|---|
| | Mulberry | *Poria cocos* peel | | | |
| Vehicle | | | | | 165.7 |
| example 1 | 250 | 50 | 5:1 | 100 | 111.7 |
| Comparative Example 1 | 200 | — | Mulberry alone | 100 | 120.1 |
| Comparative Example 2 | — | 200 | *Poria cocos* peel alone | 100 | 145.6 |
| Comparative Example 3 | 100 | 100 | 1:1 | 100 | 132.9 |
| Comparative Example 4 | 150 | 50 | 3:1 | 100 | 127.8 |
| Comparative Example 5 | 200 | 20 | 10:1 | 100 | 125.6 |
| Comparative Example 6 | 50 | 150 | 1:3 | 100 | 134.9 |
| Comparative Example 7 | 40 | 200 | 1:5 | 100 | 134.6 |
| Comparative Example 8 | 20 | 200 | 1:10 | 100 | 141.2 |
| Donepezil | | | | 1 | 168.8 |

<1-7> NGF (Nerve Growth Factor) Level Measurement

ELISA experiments were conducted to confirm the efficacy of the mixed extracts on NGF production, known to be a neuronal regeneration and differentiation activity. After the brains of normal animals in Experimental Example <1-1> were extracted, the hippocampal region was separated, and RIPA buffer was added thereto and mechanically homogenized. For NGF measurement, a high salt high detergent buffer corresponding to the weight of each brain was added and mechanically homogenized. After adding 10 µl of 4N HCl and allowing to stand for 15 minutes, NGF bound to the receptor was dissociated, 4N NaOH was added, and the mixture was allowed to stand for another 15 minutes. The supernatant was taken by centrifugation and the NGF concentration in the brain was measured using an NGF measurement kit (Millipore). The amount of NGF produced in 1 mg protein is shown in the table.

As a result, as shown in the following Table 11, it was confirmed that NGF production was significantly increased by the administration of the herbal mixed extract. Compared with Comparative Examples 1 and 2, which are sole extracts of mulberry and *Poria cocos* peel, and Comparative Examples 3 to 8, which are mixed extracts of mulberry and *Poria cocos* peel, In Example 1 according to the present invention, a mixture of mulberry and *Poria cocos* peel 5:1 showed higher NGF production promoting activity. Single herbal extracts also stimulated the production of NGF. Among them, *Poria cocos* peel extract showed relatively strong promoting effect on NGF production. In the mixed extract of botanical raw materials, when the weight ratio of *Poria cocos* peel was high, the promoting effect of NGF production was large.

Donepezil (DPZ), an acetyl cholinesterase inhibitor used in Alzheimer's disease, did not affect NGF production at a dose of 1 mg/kg.

TABLE 11

Normal animal model - NGF measurement

| | Raw material amount (kg) | | Total weight comparison | | NGF |
|---|---|---|---|---|---|
| | Mulberry | Poria cocos peel | Mulberry:Poria cocos peel weight ratio | Volume (mg/kg) | concentration (pg/mg) |
| Vehicle | | | | | 247.7 |
| example 1 | 250 | 50 | 5:1 | 100 | 395.7 |
| Comparative Example 1 | 200 | — | Mulberry alone | 100 | 256.0 |
| Comparative Example 2 | — | 200 | Poria cocos peel alone | 100 | 341.0 |
| Comparative Example 3 | 100 | 100 | 1:1 | 100 | 280.7 |
| Comparative Example 4 | 150 | 50 | 3:1 | 100 | 304.0 |
| Comparative Example 5 | 200 | 20 | 10:1 | 100 | 311.0 |
| Comparative Example 6 | 50 | 150 | 1:3 | 100 | 329.0 |
| Comparative Example 7 | 40 | 200 | 1:5 | 100 | 347.3 |
| Comparative Example 8 | 20 | 200 | 1:10 | 100 | 360.3 |
| Donepezil | | | | 1 | 258.0 |

<Experimental Example 2> Identification of Nerve Cell Protective Effect of Mulberry and *Poria cocos* Peel Mixture Extracts In Vitro <2-1> Measurement of Acetyl Cholinesterase (AChE) Activity in Nerve Cell Lines Acetyl cholinesterase inhibitors have been developed and used for various acetyl cholinesterase inhibitors because they enhance the memory capacity and improve the dementia by activating the cholinergic neurons by increasing the acetylcholine concentration in the ganglion neurotransmitter. The acetyl cholinesterase activity was measured to confirm the acetyl cholinesterase inhibitory effect of the herbal mixed extract. SH-SY5Y cells, a neuronal cell line, were purchased from KCLB (Korean Cell Line Bank). SH-SY5Y cells (1×106 cells/well) were inoculated on 6-well culture plates and cultured in DMEM/F12 (Dulbecco's modified Eagle's medium) medium containing 10% fetal bovine serum for 48 hours. After 5 days of differentiation using DMEM/F12 medium containing 10 μM retinoic acid and 3% FBS, the Examples, the Comparative Example (10 μg/ml) and the control drug (donepezil 10 μM), Aβ42 was treated. Cell lysis was performed using RIPA buffer (150 mM NaCl, 0.5% Triton X-100, 50 mM Tris-HCl, pH 7.4, 25 mM NaF, 20 mM EGTA, 1 mM DTT, 1 mM Na3VO4, protease inhibitor cocktail), And protein content was quantitated with BCA reagent purchased from Pierce. The acetyl cholinesterase enzyme activity was determined by acetylcholine as a substrate according to the Ellman method. The resulting thiocholine produced by acetyl cholinesterase was reacted with DTNB and the resulting 5-thio-2-nitrobenzoate was determined by measuring the absorbance change at 405 nm.

As a result, as shown in Table 12 below, it was confirmed that the acetyl cholinesterase activity increased by the beta amyloid treatment was normalized by the administration of the herbal mixed extract. Compared with Comparative Examples 1 and 2 which are the sole extracts of mulberry and *Poria cocos* peel and Comparative Examples 3 to 8 which are mixed extracts of mulberry and *Poria cocos* peel, The mixture of mulberry and *Poria cocos* peel 5:1 of Example 1 according to the present invention showed excellent acetyl cholinesterase activity inhibitory activity. The single herbal extracts of Comparative Examples 1 and 2 exhibited slight acetyl cholinesterase inhibitory action, but both single herbal extracts showed lower efficacy than the herbal mixed extracts. The inhibitory effect of herbal extracts was similar to that of Donepezil (DPZ) 10 μM, which is an acetyl cholinesterase inhibitor and used in Alzheimer's disease.

TABLE 12

Neuronal cell line model - acetyl cholinesterase activity

| | Raw material amount (kg) | | Total weight comparison | | Acetyl cholinesterase activity (mU/mg protein) |
|---|---|---|---|---|---|
| | Mulberry | Poria cocos peel | Mulberry:Poria cocos peel weight ratio | Volume (μg/ml) | |
| Normal | | | | | 8.94 |
| Vehicle | | | | | 13.54 |
| example 1 | 250 | 50 | 5:1 | 10 | 5.64 |
| Comparative Example 1 | 200 | — | Mulberry alone | 10 | 9.84 |
| Comparative Example 2 | — | 200 | Poria cocos peel alone | 10 | 7.23 |
| Comparative Example 3 | 100 | 100 | 1:1 | 10 | 8.54 |
| Comparative Example 4 | 150 | 50 | 3:1 | 10 | 6.32 |
| Comparative Example 5 | 200 | 20 | 10:1 | 10 | 7.32 |
| Comparative Example 6 | 50 | 150 | 1:3 | 10 | 8.11 |
| Comparative Example 7 | 40 | 200 | 1:5 | 10 | 8.32 |
| Comparative Example 8 | 20 | 200 | 1:10 | 10 | 7.64 |
| Donepezil | | | | 10 (μM) | 5.38 |

<2-2> Cell Protection Effect in Nerve Cell Line

The cytoprotective effect of herbal mixed extracts was measured using a MTT (3-(4,5-Dimethylthiazol-2-yl)-2,5-Diphenyltetrazolium Bromide) assay in a model that causes toxicity to nerve cell lines by artificially aggregated Aβ$_{42}$. SH-SY5Y cells (1×10$^4$ cells/well) were inoculated into 96-well culture plates and cultured in DMEM/F12 (Dulbecco's modified Eagle's medium: nutrient mixture F-12) containing 10% fetal bovine serum for 48 hours. After 5 days of differentiation using DMEM/F12 medium containing 10 μM retinoic acid and 3% 1-BS, 6 hours after the treatment of the Examples, the Comparative Example and the control drug (donepezil 10 μM), Aβ$_{42}$ was treated for a total of 48 hours, and after 4 hours of treatment with 2 mg/ml MTT, Formazone was dissolved in DMSO and absorbance was measured at 590 nm.

As a result, it was confirmed that the cytotoxicity induced by beta amyloid treatment was inhibited by the herbal mixed extract administration as shown in Table 13 below. Compared with Comparative Examples 1 and 2 which are solely extracts of mulberry and *Poria cocos* peel and Comparative Examples 3 to 8 which are mixed extracts of mulberry and *Poria cocos* peel, mulberry, *Poria cocos* peel 5:1 mixture showed excellent cytoprotective effect. Donepezil (DPZ), an acetyl cholinesterase inhibitor used in Alzheimer's disease, showed a low level of cytoprotective activity at a dose of 10 μM.

TABLE 13

Neuronal cell model - MTT measurement value

| | Raw material amount (kg) | | Total weight comparison | Volume (μg/ml) | MTT measurement value (% of Normal) |
|---|---|---|---|---|---|
| | Mulberry | Poria cocos peel | Mulberry:Poria cocos peel weight ratio | | |
| Normal | | | | | 100.0 |
| Vehicle | | | | | 56.2 |
| example 1 | 250 | 50 | 5:1 | 10 | 89.3 |
| Comparative Example 1 | 200 | — | Mulberry alone | 10 | 64.3 |
| Comparative Example 2 | — | 200 | Poria cocos peel alone | 10 | 82.3 |
| Comparative Example 3 | 100 | 100 | 1:1 | 10 | 68.9 |
| Comparative Example 4 | 150 | 50 | 3:1 | 10 | 72.3 |
| Comparative Example 5 | 200 | 20 | 10:1 | 10 | 79.3 |
| Comparative Example 6 | 50 | 150 | 1:3 | 10 | 66.4 |
| Comparative Example 7 | 40 | 200 | 1:5 | 10 | 68.9 |
| Comparative Example 8 | 20 | 200 | 1:10 | 10 | 79.4 |
| Donepezil | | | | 10 (μM) | 65.3 |

<2-3> Measurement of Phosphorylated Tau in Neuronal Cell Lines

Phosphorylated tau levels were measured in order to confirm the inhibitory effect of crude herbal extracts on tau hyper-phosphorylation. SH-SY5Y cells (1×106 cells/well) were seeded in 6-well culture plates and cultured in DMEM/F12 (Dulbecco's modified Eagle's medium) medium containing 10% FBS (fetal bovine serum) for 48 hours. After 5 days of differentiation using DMEM/F12 medium containing 10 μM retinoic acid and 3% FBS, After 6 hours of treatment with the example, comparative example (10 μg/ml) and a control drug (donepezil 10 μM), $A\beta_{42}$ was treated and cultured for a total of 48 hours. After cell lysis using RIPA buffer, the protein content was quantitated with BCA reagent purchased from Pierce. The phosphorylated tau was measured using human Tau [pS199] enzyme-linked immunosorbent assay (ELISA) KIT purchased from Invitrogen.

As a result, it was confirmed that the increase of tau phosphorylation induced by the beta amyloid treatment was suppressed by the herbal mixed extract as shown in Table 14 below. Compared with Comparative Examples 1 and 2, which are sole extracts of mulberry and Poria cocos peel, and Comparative Examples 3 to 8, which are mixed extracts of mulberry and Poria cocos peel, the tau phosphorylation inhibitory effect was excellent in the mixture of Example 1 mulberry and Poria cocos peel 5:1. In particular, the effect of inhibiting tau phosphorylation was significantly increased by the mixed extracts when compared to the mulberry and Poria cocos peel alone extracts. Donepezil (DPZ), an acetyl cholinesterase inhibitor used in Alzheimer's disease, did not show any inhibitory effect on tau phosphorylation at a dose of 10 μM.

TABLE 14

Neuronal cell model - Tau phosphorylation measurement

| | Raw material amount (kg) | | Total weight comparison Mulberry:Poria cocos peel weight ratio | Volume (μg/ml) | Phosphorus tau pg/g protein |
|---|---|---|---|---|---|
| | Mulberry | Poria cocos peel | | | |
| Normal | | | | | 1197 |
| Vehicle | | | | | 1684 |
| example 1 | 250 | 50 | 5:1 | 10 | 864 |
| Comparative Example 1 | 200 | — | Mulberry alone | 10 | 1579 |
| Comparative Example 2 | — | 200 | Poria cocos peel alone | 10 | 1021 |
| Comparative Example 3 | 100 | 100 | 1:1 | 10 | 1324 |
| Comparative Example 4 | 150 | 50 | 3:1 | 10 | 1027 |
| Comparative Example 5 | 200 | 20 | 10:1 | 10 | 1198 |
| Comparative Example 6 | 50 | 150 | 1:3 | 10 | 1318 |
| Comparative Example 7 | 40 | 200 | 1:5 | 10 | 1225 |
| Comparative Example 8 | 20 | 200 | 1:10 | 10 | 1150 |
| Donepezil | | | | 10 (μM) | 1699 |

<2-4> Nerve Growth Factor (NGF) Level Measurement in Nerve Cell Lines

NGF levels were measured in order to determine the mechanism of cognitive improvement of the herbal mixed extracts. SH-SY5Y cells (1×106 cells/well) were inoculated on 6-well culture plates and cultured in DMEM/F12 (Dulbecco's modified Eagle's medium) medium containing 10% fetal bovine serum for 48 hours. After 5 days of differentiation using DMEM/F12 medium containing 10 μM retinoic acid and 3% FBS, to this, the example, comparative example (10 μg/ml) and control drug (donepezil 10 μM) were treated. Cells were lysed using RIPA buffer, and protein content was quantitated with BCA reagent purchased from Pierce. NGF levels were measured using a beta-nerve growth factor human enzyme-linked immunosorbent assay (ELISA) KIT purchased from Abcam.

As a result, as shown in Table 15, it was confirmed that the herbal mixed extract increased NGF production. At this time, beta amyloid did not affect NGF production. As a result of comparing the action of NGF production of single herbal extracts, the efficacy of Poria cocos peel extract was high. Among the herbal mixed extracts, 5:1 combination was the most effective.

Donepezil (DPZ), which is used as an acetylcholinesterase inhibitor in Alzheimer's disease, did not show the effect of promoting NGF production at a dose of 10 μM.

TABLE 15

Nerve cell model - NGF measurement

| | Raw material amount (kg) | | Total weight comparison | Volume (μg/ml) | NGF (pg/g protein) |
|---|---|---|---|---|---|
| | Mulberry | Poria cocos peel | Mulberry:Poria cocos peel weight ratio | | |
| Normal | — | — | — | — | 438 |
| Vehicle | — | — | — | — | 402 |
| example 1 | 250 | 50 | 5:1 | 10 | 774 |

TABLE 15-continued

Nerve cell model - NGF measurement

| | Raw material amount (kg) | | Total weight comparison | | |
|---|---|---|---|---|---|
| | Mulberry | Poria cocos peel | Mulberry:Poria cocos peel weight ratio | Volume (μg/ml) | NGF (pg/g protein) |
| Comparative Example 1 | 200 | — | Mulberry alone | 10 | 433 |
| Comparative Example 2 | — | 200 | Poria cocos peel alone | 10 | 696 |
| Comparative Example 3 | 100 | 100 | 1:1 | 10 | 453 |
| Comparative Example 4 | 150 | 50 | 3:1 | 10 | 578 |
| Comparative Example 5 | 200 | 20 | 10:1 | 10 | 454 |
| Comparative Example 6 | 50 | 150 | 1:3 | 10 | 488 |
| Comparative Example 7 | 40 | 200 | 1:5 | 10 | 533 |
| Comparative Example 8 | 20 | 200 | 1:10 | 10 | 655 |
| Donepezil | — | — | — | 10 (μM) | 421 |

As described above, the extract of mulberry which is the material of the herbal mixed extract of the present invention appears to promote the survival of the neuron and to activate its function by removing beta amyloid which is considered to be a major cause of Alzheimer's dementia. *Poria cocos* peel extract, another material, is thought to be superior to nerve cell protection efficacy through promotion of NGF production especially, known as a neuronal protective factor. In addition, each herbal extract did not exhibit high efficacy in inhibiting the acetyl cholinesterase inhibitory effect, which is currently the major mechanism of action of drugs for Alzheimer's dementia. However, when they were mixed, the efficacy was increased. These results suggest that the extracts of mulberry and *Poria cocos* peel protect neurons and synergistically increase their memory capacity by different mechanisms. Especially, when they are mixed at a weight ratio of 5:1, it is considered that the efficacy is excellent.

Therefore, the herbal mixed extract according to the present invention inhibits the onset or progress of the disease by inhibiting beta amyloid production and tau phosphorylation, which cause degenerative brain diseases by causing neuronal cell death, and enhances memory ability by inhibiting acetylcholine esterase. It also promotes the production of NGF, which promotes neuronal protection and neural differentiation. Therefore, it can be usefully used for prevention, amelioration and treatment of progressive dementia due to gradual killing of neurons such as Alzheimer's dementia and Creutzfeldt-Jakob disease, Huntington's disease, multiple sclerosis, Guilin-Barre syndrome, Parkinson's disease, Lou Gehrig's disease. It may also be useful for the prevention, amelioration and treatment of degenerative neurological disorders including posture and movement disorders, progressive ataxia, muscular atrophy and weakness, sensory and motor disorders and so on.

Hereinafter, a preparation example of a composition containing a crude drug extract of Example 1 of the present invention will be described. However, it should be understood that the present invention is not intended to be limited thereto but is specifically described.

Preparation Example 1: Preparation of Injections

| Example 1 Extract | 100 mg |
|---|---|
| Sodium Metabisulfite | 3.0 mg |
| Methylparaben | 0.8 mg |
| Propylparaben | 0.1 mg |
| Sterilized distilled water for injection | Proper amount |

The above ingredients are mixed and made into 2 ml by a usual injection preparation method, after that filled in a 2 ml ampoule and sterilized to prepare an injection.

Preparation Example 2: Preparation of Tablets

| Example 1 Extract | 200 mg |
|---|---|
| Lactose | 100 mg |
| Starch | 100 mg |
| Magnesium stearate | Proper amount |

The above components are mixed and tablets are prepared by tableting according to the conventional tablet preparation method.

Preparation Example 3: Preparation of Capsules

| Example 1 Extract | 100 mg |
|---|---|
| Lactose | 50 mg |
| Starch | 100 mg |
| Talc | 2 mg |
| Magnesium stearate | Proper amount |

The above components are mixed and filled in gelatin capsules according to the conventional preparation method of capsules to prepare capsules.

Preparation Example 4: Preparation of Liquid Agent

| Example 1 Ethanol extract | 1000 mg |
|---|---|
| sugar | 20 g |
| High Fructose Corn | 20 g |
| Lemon incense | Proper amount |
| After adding purified water, the total liquid volume | 100 ml |

The above components are mixed according to the usual method for producing a liquid preparation, filled in 100 ml of a brown bottle and sterilized to prepare a liquid preparation.

The invention claimed is:

1. A method of increasing the production of nerve growth factor (NGF) in a subject having Alzheimer's Dementia, comprising administering a composition comprising an extract of a mixture which comprises (i) mulberry and (ii) *Poria cocos* peel to the subject, wherein the mixture is in a weight ratio of 5:1 of the mulberry to the *Poria cocos* peel, and wherein the composition does not comprise *Poria cocos* wolf and Jeokbokryeong.

2. The method of claim 1, wherein the composition improves cognitive abilities in the subject.

3. The method of claim 1, wherein the composition enhances memory in the subject.

4. A method of treating or ameliorating Alzheimer's Dementia in a subject in need thereof, comprising administering a composition comprising an extract of a mixture which comprises (i) mulberry and (ii) *Poria cocos* peel to the subject, wherein the mixture is in a weight ratio of 5:1 of the mulberry to the *Poria cocos* peel, and wherein the composition does not comprise *Poria cocos* wolf and Jeokbokryeong.

5. A method of decreasing the production of beta amyloid, reducing acetyl cholinesterase activity, and/or reducing tau phosphorylation in a subject having Alzheimer's Dementia comprising administering an extract of a mixture which comprises (i) mulberry and (ii) *Poria cocos* peel to the subject, wherein the mixture is in a weight ratio of 5:1 of the mulberry to the *Poria cocos* peel, and wherein the composition does not comprise *Poria cocos* wolf and Jeokbokryeong.

6. The method of claim 5, wherein the composition improves cognitive abilities in the subject.

7. The method of claim 5, wherein the composition enhances memory in the subject.

* * * * *